United States Patent
Brown et al.

(10) Patent No.: US 6,217,562 B1
(45) Date of Patent: Apr. 17, 2001

(54) WATER-DISPERSIBLE DISPOSABLE ENCLOSURE

(76) Inventors: Malcolm David Brown, 87 the Lammas, Mundford, Norfolk, 1P26 5DS; Barry John Muncaster, 8 Burling Walk, Milton, Cambs CB4 GDX, both of (GB)

(*) Notice: Subject to any disclaimer, the term of this patent is extended or adjusted under 35 U.S.C. 154(b) by 0 days.

(21) Appl. No.: 08/952,915

(22) PCT Filed: May 24, 1996

(86) PCT No.: PCT/GB96/01267

§ 371 Date: Mar. 5, 1998

§ 102(e) Date: Mar. 5, 1998

(87) PCT Pub. No.: WO96/37171

PCT Pub. Date: Nov. 28, 1996

(30) Foreign Application Priority Data

May 25, 1995 (GB) .................................................. 9510596
Jan. 27, 1996 (GB) .................................................. 9601690

(51) Int. Cl.⁷ ............................................................ A61M 1/00
(52) U.S. Cl. ............................................. 604/327; 604/317
(58) Field of Search ....................................... 604/327, 332; 383/1; 428/35.2, 36.5

(56) References Cited

U.S. PATENT DOCUMENTS

| | | | |
|---|---|---|---|
| 4,868,024 | * | 9/1989 | Cross et al. ............................. 604/332 |
| 5,009,647 | * | 4/1991 | Cross et al. .............................. 383/1 |
| 5,427,794 | * | 6/1995 | Miles ................................... 424/405 |
| 5,429,874 | * | 7/1995 | Van Putte ............................. 428/35.4 |

FOREIGN PATENT DOCUMENTS

94/26727 * 11/1997 (WO) ................................. 514/222.8

* cited by examiner

*Primary Examiner*—Kim M. Lewis
(74) *Attorney, Agent, or Firm*—Synnestvedt & Lechner LLP

(57) ABSTRACT

A water-dispersible disposable enclosure, such as an ostomy pouch or urinary incontinence pouch, which is adapted for flushing down the bowl of a water closet and is formed of a material that is, at least at the time of disposal into a water closet bowl, combined with a water activated exothermic reagent that raises the temperature of the enclosure or the water that comes into contact with the enclosure, prior to or upon placement in the water closet bowl, to a level at which the material melts, dissolves or otherwise disperses for ease of flushing.

14 Claims, 2 Drawing Sheets

WATER-DISPERSIBLE DISPOSABLE ENCLOSURE

FIELD OF THE INVENTION

The present invention relates to the field of water-dispersible disposable health care goods and particularly but not exclusively to ostomy and faecal and urinary incontinence pouches.

BACKGROUND OF THE INVENTION

There are a surprisingly large number of patients, most notably in the UK and USA, who have undergone major surgery of the digestive track and are reliant upon a colostomy or ileostomy pouch to collect unabsorbed or excreted waste material from the digestive tract. For such patients use of these pouches represents a very considerable hardship and invariably involves wearing the pouch for many hours on end and awkward fitment and removal at frequent intervals with the further problem that upon removal of the pouch it must then be disposed of.

Fitment and removal of an ostomy pouch is generally carried out within the confines of a water closet and the pouch then is either emptied of its contents into the water closet bowl with the pouch then being binned or sealed away for carriage to a remote waste disposal unit or the pouch is adapted to be flushed away, following emptying or complete with its contents.

A variety of different designs of ostomy bag exist that are adapted for flushing and which are, for example, either adapted to be softened in the cold water of the toilet bowl or dispersed in hot water such as arises in the sludge digester of a sewage treatment plant and as disclosed in, for example, GB 2 290 968.

For those designs that are adapted to disperse or biodegrade in the environment of a sludge digester this does not, of course, facilitate the flushing of the product or its transit through the soil pipe and sewage drains. Other product designs are adapted to disperse upon contact with cold water when the pH of that water is adjusted to a level at which the material of the pouch is cold water soluble. Examples of the latter include U.S. Pat. No. 5,417,677 and GB 2 195 919. Such prior art systems of flushing disposal of ostomy and incontinence pouches are, however, not necessarily swift methods of disposal or do not allow for complete dispersal prior to flushing or, furthermore, require the carrying of potentially dangerous acid or alkali by the patient/wearer.

It is a general objective of the present invention to provide an ostomy/incontinence pouch or bag that is rapidly dispersible for flushing down a water closet without necessitating carrying of acidic or alkaline substances to facilitate the dispersion.

SUMMARY OF THE INVENTION

According to a first aspect of the present invention there is provided a water-dispersible disposable enclosure such as an ostomy pouch or urinary incontinence pouch which is adapted for flushing down the bowl of a water closet and is formed of a material that at the time of disposal into a water closet bowl is combined with a water-activated exothermic reagent that raises the temperature of the enclosure or the water that comes into contact with the enclosure, prior to or upon placement in the water closet bowl, to a level at which the material melts, dissolves or otherwise disperses for ease of flushing.

The preferred material of the enclosure is a hot water soluble material such as hot water soluble polyvinyl alcohol and the preferred water-activated exothermic reagent is silica gel, aluminium chloride or calcium chloride. Each of these water-activated exothermic reagents is capable of raising the localised temperature of the aqueous media within the enclosure or the immediately surrounding water to a level of 60° C. or 80° C. necessary to dissolve or disperse the hot water soluble polyvinyl alcohol from which the enclosure is formed or to heat and melt an enclosure formed of low melting point material such as 60° C. MP polycaprolactone film.

It will be appreciated that the material forming the enclosure is not soluble, dispersible or meltable at body temperature and is, therefore, not vulnerable to degradation by the warm bodily liquids that it is adapted to store. Therefore, by provision of the water-activated exothermic reagent only upon the external surface of the enclosure the enclosure is vulnerable only to externally applied water/aqueous media. Alternatively, by introducing the exothermic reagent into the enclosure only at time of disposal it retains its integrity until disposal.

The water-activated exothermic reagent may be coated upon the external surface of the enclosure at the time of manufacture and may be applied continuously or discontinuously as necessary to achieve adequate disintegration of the product upon disposal. For the greater comfort of the user, depending upon the nature of reagent used, the reagent may be best applied substantially solely to the face of the pouch/enclosure that is remote from the wearer, rather than adjacent the skin of the wearer.

The water-activated exothermic reagent may be applied at the time of disposal by means of a spray, wipe or applicator pen or may be incorporated in or on the enclosure, for example inside a sachet which is punctured or ruptured by the action of a tool or force after the useful life of the enclosure or within a pocket on the enclosure that is cold water soluble to release the reagent upon placements in the bowl of the water closet, or may be introduced into the enclosure through a valve.

According to a second aspect of the present invention there is provided a water-dispersible disposable enclosure such as an ostomy pouch or urinary incontinence pouch, which enclosure is formed from a material that is rapidly soluble in an organic solvent and which solvent is introduced into, released onto or coated onto the external surface of the enclosure at the time of disposal into a water closet bowl.

The present invention also provides a method of disposal of a water disposable enclosure of the second aspect of the invention which includes the step of applying solvent to the enclosure, internally or externally by a spray or other applicator means immediately prior to flushing the enclosure down the water closet.

Preferred examples of organic solvent soluble material forming the enclosure include polycaprolactone film and gelatinised starch film, both of which are soluble in the solvent N-methyl pyrrolidone. For this purpose, N-methyl pyrrolidone is a preferred solvent since it is not only very effective but also both biodegradable and non-inflammable.

According to a third major aspect of the present invention there is provided a water-dispersible disposable enclosure such as an ostomy pouch or urinary incontinence pouch, which enclosure is formed from a material that will dissolve or otherwise disperse in aqueous media as a result of salt replacement, the salt being applied to the external surface of the enclosure at the time of disposal into a water closet bowl. A particular preferred example of such material and salt are a film of calcium alginate that will dissolve in presence of aqueous sodium salt due to relative solubility of sodium alginate. Therefore, by providing sodium chloride in association with the disposable enclosure formed of calcium alginate, either stored in a pocket or sachet on the enclosure that is ruptured or dissolved at time of disposal or by independently applying then sodium salt to the enclosure at time of disposal, the sodium salt will dissolve in the water of the water closet bowl and replace the calcium of the calcium alginate film to render the enclosure cold water soluble.

Where the enclosure is an ostomy pouch it is suitably of the type which has a 2-part attachment to the wearer, having a base portion that semi-permanently mounts around the abdominal opening in the patient and a corresponding flange. on the pouch that cooperatively engages with the base portion, the flange being of a substantially rigid construction and in accordance with a further aspect of the present invention being formed of a rigid grade of the material of any of the previous aspects of the present invention, ie one which is meltable, soluble or dispersible as described herein above, or which is slowly cold-water soluble ie dissolves in cold water over a period of several hours as do certain grades of cold water soluble PVA.

Even where the pouch has a single-piece attachment to the wearer it is conceivable that this might also be made of the said meltable, soluble or dispersible material.

As a further improvement to the design of water-dispersible disposable enclosure of any of the previous aspects of the present invention, the enclosure is suitably at least partially formed of a material and in a configuration whereby exposure to the large volumes of water of a toilet bowl causes differential shrinkage from one region of the enclosure to another thereby tearing the enclosure apart. This may be achieved by, for example, use of strands of polyvinyl alcohol overlain upon or encased within and bonded to a base material which upon sufficient exposure of the strands to water causes shrinkage of the strands, thereby pulling the base material to which the strands are bonded apart. The strands may be formed into a matrix or a matrix may be formed that isn't strictly composed of independent strands but which nonetheless has the effect of tearing the base material and itself apart upon exposure to water.

BRIEF DESCRIPTION OF THE DRAWINGS

Preferred embodiments of the present invention will now be more particularly described, by way of example, with reference to the accompanying drawings, wherein.

DESCRIPTION OF THE PREFERRED EMBODIMENT

Figure 1:
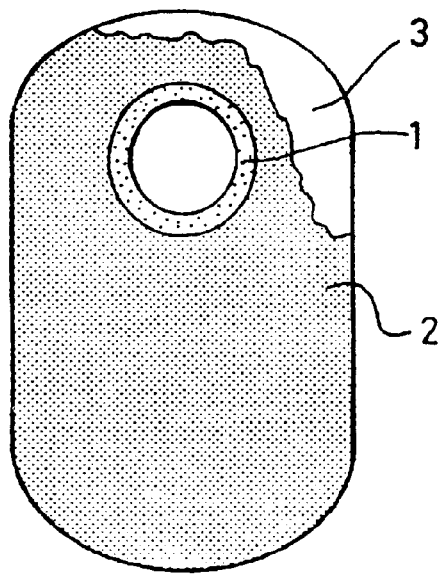
FIG. 1 is a front elevation view of an ostomy pouch coated with a water-activated exothermic reagent of the first aspect of the present invention.
Figure 2:
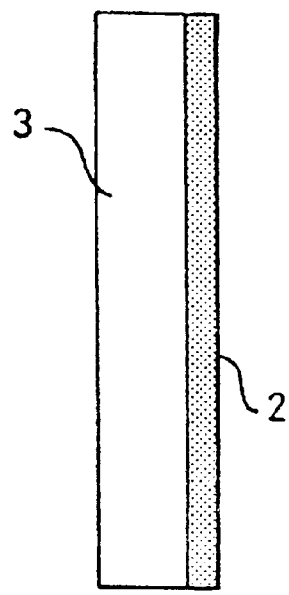
FIG. 2 is a transverse sectional view through the membrane that forms the pouch of FIG. 1.

Referring to FIGS. 1 and there is shown an ostomy pouch of broadly conventional shape and having a conventional circular rimmed aperture 1 that is adapted to be adhered to the abdominal opening of an ostomy patient for the passage of fluids from the patient as abdomen into the pouch.

Illustrated patterning 2 on the external surface of the pouch depicts an external coating 2 of a water-activated exothermic reagent covering the material 3 forming the pouch.

By way of example, the preferred pouch forming material 3 comprises a hot water soluble polyvinyl alcohol. Suitable specific examples of such polyvinyl alcohol include Vinylon 30 micron from Nippon Goshei which dissolves or disperses at 80° C.; HiSelon Type H at 40 micron from the same company which dissolves or disperses at 60° C.; and Aquafilm Type A127 at 50 micron from Aquafilm which dissolves or disperses at 60° C. All three of these polyvinyl alcohol materials have been used as the pouch-forming material 3 and when coated with a water-sensitive exothermic reagent such as aluminium chloride, calcium chloride or silica gel in small amounts sufficient to raise the localised temperature around the surface of the bag to the temperature levels for dissolution or dispersion of the material on contact with water effectively completely dissolved or dispersed the material within 2 minutes.

In this embodiment it may be desirable to use a comfort panel between the rear face of the pouch and the skin of the wearer or to ensure that the exothermic reagent coating 2 is applied only to the front face of the pouch away from the wearer. Such panel may be formed of, for example, a woven fabric of viscose or cotton bonded together by a water dispersible polyvinyl alcohol.

By way of further refinement, a protective panel may be provided to extend over the front face of the pouch to protect it from accidental exposure to substantial volumes of water during use. In this case, such a protective panel is perhaps most usefully mounted to the less frequently disposed of base portion 4 of a two part attachment pouch, such as illustrated in FIG. 6.

Figure 6:
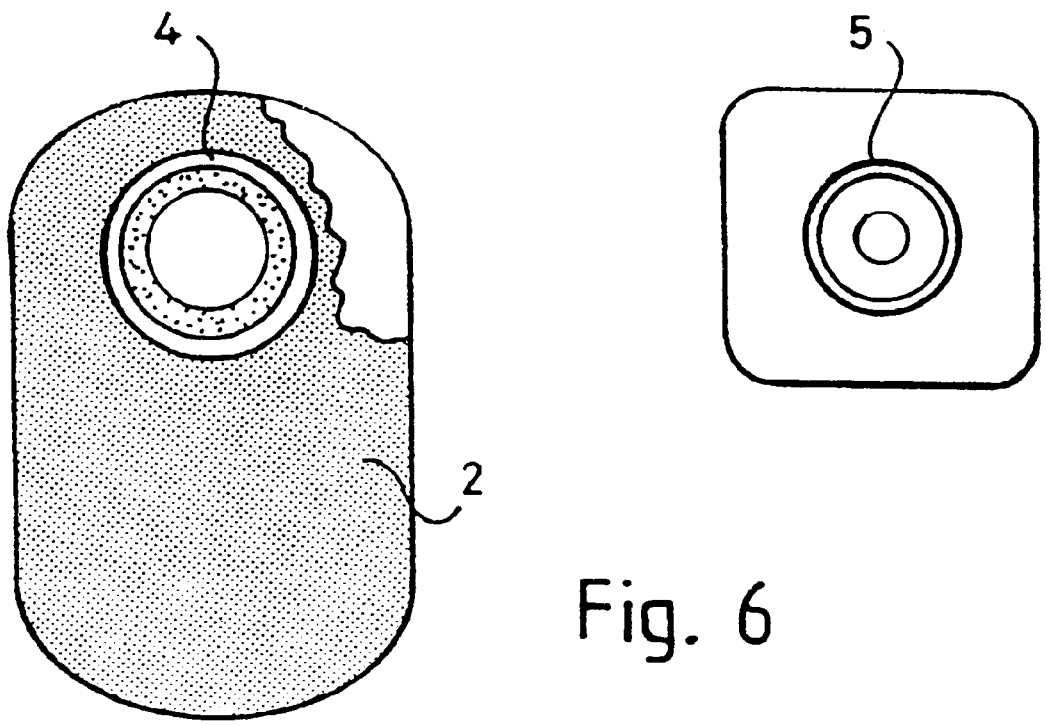
FIG. 6 is a front elevation view of an ostomy pouch having a two part attachment to the wearer.

The two part attachment in the FIG. 6 embodiment comprises the base portion 4 that adheres over the abdominal opening in the patient and a corresponding annular flange 5 that cooperatively engages with the base portion 4 to mount the pouch in fluid communication with the opening in the patient. The annular rim of the base portion 5 and the annular flange 4 of the pouch are conventionally formed of mate that are not ideally suited to flushing and that although in some cases may be softenable in contact with water generally retain their rigidity and are non-dispersible. One common material used in the prior art is keraya gum for the one part design and polyethylene or polypropylene for the two part design.

In accordance with one particular preferred embodiment of the present invention, the annular rim on that base portion and the annular flange on the pouch are suitably both formed of a water soluble dispersible material that may, for example, be a rigid grade of the material 3 used to form the pouch itself or may be a slowly cold water soluble material such a substantially rigid grade of cold water soluble polyvinyl alcohol. An example of such a polyvinyl alcohol is Ecomaty AX2000 from Nippon Goshei. As an alternative possibility, the flange and annular rim may also be formed from Mater Bi resin modified to dissolve slowly.

Turning to the second aspect of the present invention, to be rapidly dispersible for flushing, the pouch may be formed of a material 3 that is rapidly soluble in relatively small volumes or organic solvent that may be spray applied or otherwise released into or onto the pouch at time of disposal.

Examples of such pouch material 3 include 30 micron gelatinised starch film known as Mater Bi which will dissolve well within 2 minutes when combined with the solvent N Methylpyrrolodine. A further example of pouch forming material rapidly soluble in organic solvent is a film of polycaprolactone that is rapidly soluble in, for example, toluene.

Figure 3:
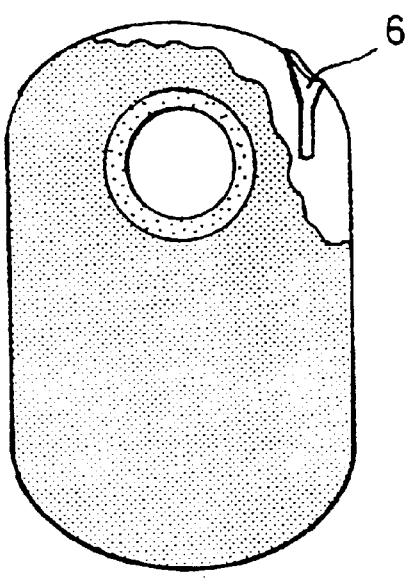
FIGS. 3 and 4 are front elevation views of pouches similar to that illustrated in FIG. 1 but respectively having a valve-gated reservoir or a sachet holding reagent for melting, dissolving, dispersing or otherwise disintegrating the pouch.
Figure 4:
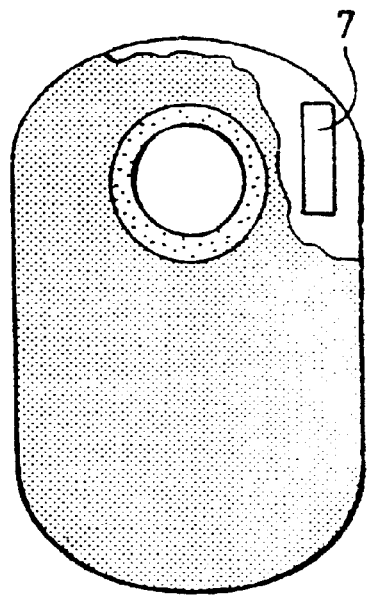
Figure 5:
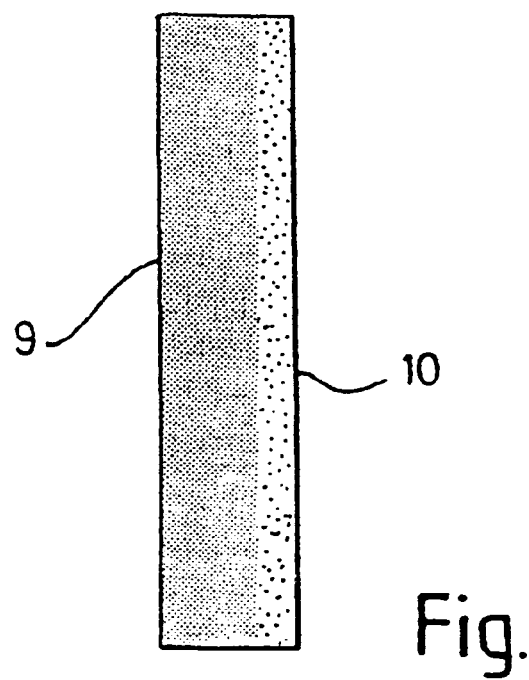
FIG. 5 is a transverse sectional view similar to that of FIG. 2 but through a woven or non-woven fabric such as viscose or cotton bonded with hot water soluble material on the internal face of the fabric.

FIGS. 3 and 4 illustrate different means for associating the solvent with the pouch. In FIG. 3 the valve 6 is provided extending into the internal cavity of the pouch to enable solvent to be introduced into the pouch at time of disposal by means of a pressurised spray or pump-action device.

In FIG. 4 a sachet 7 is provided in the wall of the pouch containing solvent that may be released upon puncturing or rupturing the sachet 7 by action of a tool or force.

Although described above with respect to a preferred arrangement in which the pouch forming material is a single film, of material such as polyvinyl alcohol, the pouch forming material may comprise a composite 9 of, for example, a woven fabric of viscose, cotton or other suitably biodegradable material that is bound together by the hot water soluble material or organic solvent soluble material 10 on its inner face or, in accordance with the third aspect of the present invention, bound together by a water soluble/dispersible material that only becomes water soluble/dispersible upon salt replacement.

By way of example of this latter aspect of the invention, the pouch is formed of or bound together by calcium alginate that is brought into contact with the water soluble sodium salt at time of disposal.

In the case of the application of a coating of water-activated exothermic reagent to hot water soluble pouch forming material, the reagent coating need not be applied continuously over the external surface of the pouch but may be laid in a grid pattern or otherwise applied so that the pouch will at least disintegrate into small enough pieces to be readily flushable. This may be satisfactory, particularly bearing in mind that the materials are generally fully biodegradable.

What is claimed is:

1. A disposable enclosure dispersible in water and a reagent, said enclosure comprising a material adapted to disperse for ease of flushing down a water closet, characterized in that the material is meltable, soluble or otherwise dispersible on contact with heat and the enclosure is provided with a water-activated exothermic reagent.

2. A disposable enclosure dispersible in water and a reagent, said enclosure comprising a material adapted to disperse for ease of flushing down a water closet, characterized in that the material is soluble or otherwise dispersible in a reagent selected from an organic solvent and a salt, and the enclosure is provided with the reagent, wherein the reagent is included separate from the enclosure.

3. The enclosure according to claim 1, wherein the reagent is a continuous or discontinuous coating on the external surface of the enclosure.

4. The enclosure according to claim 3, wherein said enclosure is wearable on a patient, said enclosure having a first face positionable adjacent to the skin of said patient and a second face remote from the skin, the reagent being applied substantially solely to said second face of said enclosure.

5. The enclosure according to claim 1, wherein the reagent is in a pocket or sachet on the enclosure, which pocket or sachet is adapted to release the reagent on disposal.

6. The enclosure according to claim 1, wherein the reagent is adapted to be applied on disposal by spray, wipe, applicator pen or other applicator means.

7. The enclosure according to claim 1, wherein the material is selected from polyvinyl alcohol, polycaprolactone, gelatinized starch and calcium alginate.

8. The enclosure according to claim 1, wherein the reagent is selected from silica gel, aluminum chloride and calcium chloride.

9. The enclosure according to claim 2, wherein the reagent is selected from N-methyl pyrrolidone and toluene.

10. The enclosure according to claim 2, wherein the reagent comprises a salt.

11. The enclosure as claimed in claim 1, which comprises an ostomy pouch that has a two-part attachment to the wearer of which at least the flange portion on the pouch that cooperatively engages with a base portion adhered to the wearer is of substantially rigid construction and is formed of a rigid grade of the material adapted to disperse according to claim 1, or which is slowly cold-water soluble.

12. An enclosure as claimed in claim 1, which is further characterized in that the enclosure is adapted to tear itself apart by shrinkage of parts of the enclosure upon contact with water.

13. A method of disposal of the enclosure of claim 1, which includes the step of applying the reagent to the enclosure, internally or externally by a spray or other applicator means, immediately prior to flushing the enclosure down the water closet.

14. The enclosure according to claim 10, wherein said salt comprises sodium chloride.

* * * * *